United States Patent
Manspeizer

(10) Patent No.: US 6,540,708 B1
(45) Date of Patent: Apr. 1, 2003

(54) POLYCENTRIC JOINT FOR INTERNAL AND EXTERNAL KNEE BRACE

(76) Inventor: Sheldon Manspeizer, 1 Autumn Ridge Rd., Pound Ridge, NY (US) 10576

( * ) Notice: Subject to any disclaimer, the term of this patent is extended or adjusted under 35 U.S.C. 154(b) by 0 days.

(21) Appl. No.: 09/506,643

(22) Filed: Feb. 18, 2000

(51) Int. Cl.$^7$ .................................................. A61F 5/00
(52) U.S. Cl. .......................................... 602/16; 602/26
(58) Field of Search .............................. 602/5, 16, 23, 602/26, 32, 36; 128/882; 623/39, 42

(56) References Cited

U.S. PATENT DOCUMENTS

| | | | |
|---|---|---|---|
| 3,748,662 A | 7/1973 | Helfet ........................ 3/1 |
| 3,801,990 A | * 4/1974 | Helfet |
| 4,523,585 A | 6/1985 | Lamb et al. .............. 128/80 |
| 4,603,690 A | 8/1986 | Skeen ...................... 128/80 |
| 4,637,382 A | 1/1987 | Walker ..................... 128/92 |
| 4,940,044 A | 7/1990 | Castillo .................... 128/80 |
| 5,230,696 A | 7/1993 | Silver et al. ............. 602/16 |
| 5,330,418 A | 7/1994 | Townsend et al. ...... 602/26 |
| 5,507,820 A | 4/1996 | Pappas ..................... 623/20 |
| 5,611,774 A | 3/1997 | Postelmans .............. 602/16 |
| 5,632,725 A | 5/1997 | Silver et al. ............. 602/26 |
| 5,871,539 A | 2/1999 | Pappas ..................... 623/20 |
| 5,928,234 A | 7/1999 | Manspeizer ............. 601/61 |

OTHER PUBLICATIONS

Billings, Annette, M.D.; Scott, David F., M.D.; Camargo, Marcelo P., M.D.; Hofmann, Aaron A., M.D., Salt Lake City, Utah: *Tibial Osteotomy with a Calibrated Osteotomy Guide, Rigid Internal Fixation and Early Motion. Long–Term Follow–Up.* J. Bone and Joint Surgery, Jan. 2000; 82–A; 70–79.

Cole, Brian J., M.D.; Harner, Christopher D., M.D.: *Degenerative Arthritis of the Knee in Active Patients: Evaluation and Management.* J. Amer. Acad. Orthop. Surg. 1999; 7: 389–402.

Coventry, M.B.; Ilstrup, D.M.; and Wallrichs, S.L.: *Proximal tibial osteotomy. A critical long–term study of eighty–seven cases.* J. Bone and Joint Surgery, Feb. 1993; 75–A; 196–201.

Draper, E.R.C.; Cable, J.M.; Sanchez–Ballester, J.; Runt, N.; Robinson, J.R.; Strachan, R.K.: *Improvement in Function after Valgus Bracing of the Knee. An Analysis of Gait Symmetry.* J. Bone and Joint Surgery, Sep. 2000; 82–B: 1001–1005.

France, E. Paul, Ph.D.; Paulos, Lonnie E., M.D.: *Knee Bracing.* J. Amer. Acad. Orthop. Surg. 1994; 2: 281–287.

Magyar, G.; Toksvig–Larsen, S.; Lindstrand, A.: *Hemicallotasis Open–Wedge Osteotomy for Osteoarthritis of the Knee. Complications in 308 Operations.* J. Bone and Joint Surgery, May 1999; 81–B: 449–451.

(List continued on next page.)

*Primary Examiner*—Denise M. Pothier
(74) *Attorney, Agent, or Firm*—Lerner, David, Littenberg, Krumholz & Mentlik, LLP

(57) ABSTRACT

The present invention relates to an internal or external knee brace having a polycentric joint that enables control of a predetermined helicoidal motion and which permits compression and distraction of the knee joint. The knee brace includes a femoral component having a femoral joint member having at least one mating surface with a predetermined contour, and a stem projecting from the femoral joint member for attachment to the femur. The knee brace further includes a tibial component having a tibial joint member having at least one bearing surface for contact with the mating surface of the femoral component, and a stem projecting from the tibial joint member for attachment to the tibia. The joint members are arranged in a mounting member which has a spring or other resilient member located at one end which biases the tibial component toward the femoral component. The femoral component is fixed in the mounting member and the tibial component is rotatable relative to the fixed femoral component.

19 Claims, 13 Drawing Sheets

OTHER PUBLICATIONS

O'Driscoll, Shawn W., Ph.D. M.D., F.R.C.S., Rochester, Minnesota: *The Healing and Regeneration of Articular Cartilage*. J. Bone and Joint Surgery, Dec. 1998; 80–A; 1795–1812.

Salter, R.B.; Simmonds, D.F.; Malcolm, B.W.; Rumble, E.J,; MacMichael, D.; and Clements, N.D.: *The Biological Effect of Continuous Passive Motion on the Healing of Full–thickness Defects in Articular Cartilage. An experimental investigation in the rabbit*. J. Bone and Joint Surgery, Dec. 1980; 62–A; 1232–1251.

Bledsoe, Gary, *Principles of Lower Extremity Bracing*, Orthopedics Today, (2001).

Bull, A.M.J. & Amis, A.A., *Knee Joint Motion: Description and Measurement*, Proc. Instn. Mech. Engrs. [H] 212(5):357–72 (1998).

Jonsson, H. & Karrholm, J., *Three–Dimensional Knee Joint Movements During a Step–Up: Evaluation after Anterior Cruciate Ligament Rupture*, J. Ortho. Res. 12(6):769–79 (1994).

Karrholm et al., *Kinematics of Successful Knee Prostheses During Weight–Bearing: Three–Dimensional Movements and Positions of Screw Axes in the Tricon–M and Miller–Galante Designs*, Knee Surg. Sports Traumatol. Arthrosc. 2(1):50–9 (1994).

Weidenhielm et al., *Knee Motion after Tibial Osteotomy for Arthorosis. Kinematic Analysis of 7 Patients*, Acta Orthop. Scand. 64(3):317–19 (1993).

Hart et al., *A Finite Helical Axis as a Landmark for Kinematic Reference of the Knee*, J. Biomech. Engr. 113(2):215–22 (1991).

Blankevoort et al., *Helical Axes of Passive Knee Joint Motions*, J. Biomech. 23(12):1219–29 (1990).

Shiavi et al., *Helical Motion Analysis of the Knee—II. Kinematics of Uninjured and Injured Knees During Walking and Pivoting*, J. Biomech. 20(7):653–65 (1987).

Shiavi et al., *Helical Motion Analysis of the Knee—I. Methodology for Studying Kinematics During Locomotion*, J. Biomech. 20(5)459–69 (1987).

Kaneda et al., *Experimental Study on External Tibial Rotation of the Knee*, Am. J. Sports. Med. 25(6):796–800 (1997).

\* cited by examiner-

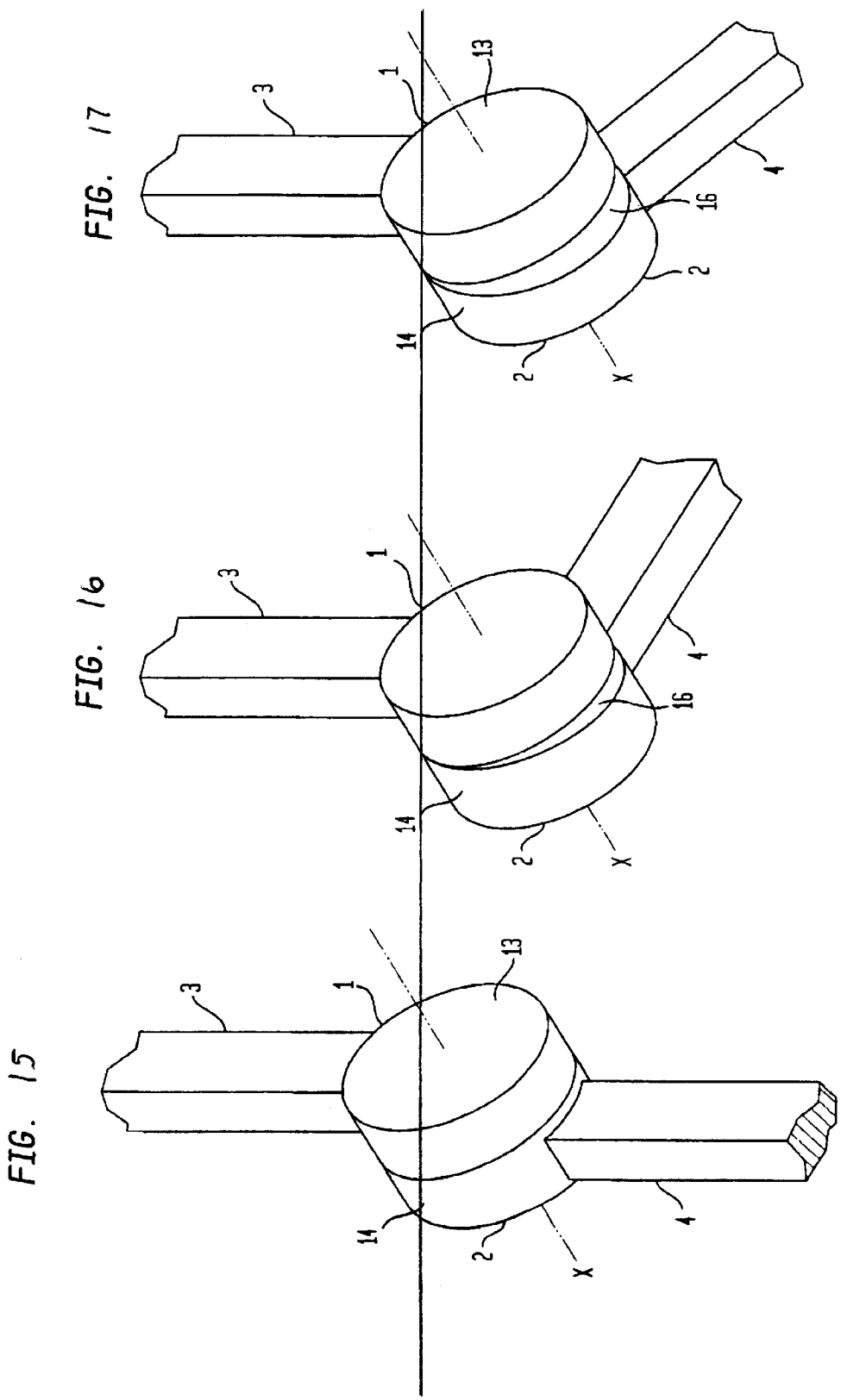

POLYCENTRIC JOINT FOR INTERNAL AND EXTERNAL KNEE BRACE

FIELD OF THE INVENTION

The present invention relates generally to orthotics, and more specifically to a polycentric joint for use in an internal or external knee brace.

BACKGROUND OF THE INVENTION

The physiological motion of the human knee involves an extremely complex "polycentric" motion wherein the center of rotation of the tibia with respect to the femur varies as a function of the angle of rotation. This motion is caused by the simultaneous movements of the interacting surfaces involved in articulation of the knee, including: (1) rotation of the tibia relative to the femur about a vertical axis; (2) movement between the femoral and tibial parts about a horizontal, anterior-posterior axis; and (3) sliding and anterior-posterior rolling of ends of the femoral and tibial parts in an anterior-posterior plane. The physiological motion of the tibia relative to the femur is further complicated by the three-dimensional component of motion outside the sagittal plane, and by the contribution of ligaments, tendons and cartilage structure.

As a result of contributions from all these factors, a given point on the tibia typically traces a complex, nonlinear curve in the three-dimensional coordinate system of the femur. This curve has been described as a helicoidal motion, which is a description of displacement of the moving body—the tibia—relative to the fixed body—the femur—as rotation about, and translation along a screw axis. See A. M. Bull & A. A. Amis, *Knee Joint Motion: Description and Measurement*, Proc Inst Mech Eng [H] 212 (5):357–72 (1998); H. Jonsson & J. Karrholm, *Three-dimensional Knee Joint Movements During a Step-up: Evaluation After Anterior Cruciate Ligament Rupture*, J Orthop Res 12(6):769–79 (1994); J. Karrholm et al., *Kinematics of Successful Knee Prostheses During Weight-bearing: Three-dimensional Movements and Positions of Screw Axes in the Tricon-M and Miller-Galante Designs*, Knee Surg Sports Traumatol Arthrosc 2 (1):50–9 (1994); L. Weidenhielm, *Knee Motion After Tibial Osteotomy for Arthrosis. Kinematic Analysis of 7 Patients*, Acta Orthop Scand 64 (3):317–19 (1993); R. A. Hart et al., *A Finite Helical Axis as a Landmark for Kinematic Reference of the Knee*, J Biomech Eng 113 (2):215–22 (1991); L. Blankevoort et al., *Helical Axes of Passive Knee Joint Motions*, J Biomech 23 (12):1219–29 (1990); R. Shiavi et al., *Helical Motion Analysis of the Knee—II. Kinematics of Uninjured and Injured Knees During Walking and Pivoting*, J Biomech 20 (7):653–65 (1987); R. Shiavi et al., *Helical Motion Analysis of the Knee—I. Methodology for Studying Kinematics During Locomotion*, J Biomech 20 (5):459–69 (1987); Y. Kaneda et al., *Experimental Study on External Tibial Rotation of the Knee*, Am J Sports Med 25 (6):796–800 (1997).

Knee joint endoprosthesis which purportedly replicate the complex polycentric motion of the knee have been proposed. Pappas, U.S. Pat. No. 5,507,820 and Helfet, U.S. Pat. No. 3,748,662, for example, disclose ball and socket knee endoprosthesis in which the ball-like femoral component engages an articulating helicoidal socket-like tibial component to control a complex three-dimensional movement.

Knee support braces which purportedly replicate the complex motion of the knee have also been proposed. Postelmanns, U.S. Pat. No. 5,611,774, for example, discloses a slotted, knee support brace which includes femoral and tibial rods that widen at one end to form corresponding shells. The shells are linked to each other using a pair of guide slots having a predetermined curvature and a pair of studs projecting laterally with respect to the surface of each shell. The femoral and tibial shells also have curved outer surfaces of different predetermined curvature. In the assembled state, the stud of the femoral joint is positioned in the slot of the tibial joint, and vice-versa. The shells are then held together by nuts which are screwed onto the projecting ends of the studs. During flexion, the tibial stud moves near to one end of the slot, following the defined curvature of the slot, and the second stud follows the path defined by the tibial slot. Because the femoral and tibial shells have curved outer surfaces, during flexion, the femoral and tibial shells are not in contact with each other over the whole of their surface. Thus, at all times, the femoral and tibial shells are connected at at least three points, a point determined by the curvatures of the shell surfaces, and two points where the studs interact with the slots.

One disadvantage of the Postelmanns' knee brace and other traditional knee braces, however, is that they do not readily withstand compression and distraction forces. It has been found that many knee conditions significantly benefit from both polycentric motion as well as compression and distraction of the knee joint. Therefore, there is a need in the art for a knee brace which is capable of controlling a complex polycentric motion but which is also capable of withstanding compression and distraction forces.

SUMMARY OF THE INVENTION

The present invention relates to an internal or external knee brace having a polycentric joint that enables control of a predetermined helicoidal motion and which permits compression and distraction of the knee joint. In an apparatus according to the present invention, the knee brace includes a femoral component including a femoral joint member having at least one mating surface with a predetermined contour, and a stem projecting from the femoral joint member for attachment to the upper leg. The knee brace further includes a tibial component including a tibial joint member having at least one bearing surface for contact with the mating surface of the femoral joint member, and a stem projecting from the tibial joint member for attachment to the lower leg. The femoral joint and tibial joint members are in juxtaposition and aligned on opposite sides of a vertical, anterior-posterior plane in a mounting member. At least a portion of the femoral joint member is fixed to the mounting member. The tibial joint member, on the other hand, is rotatable relative to the fixed femoral joint member within the mounting member. The mounting member further includes a resilient member, such as a spring, which is used to bias the tibial joint member toward the femoral joint member.

During rotation of the knee, the bearing surface of the tibial joint member follows the predetermined contour of the mating surface of the femoral joint member resulting in medial or lateral displacement of the tibial component relative to the fixed femoral component as a function of the position of the knee. The displacement is characterized as a helicoidal path during flexion of the knee and a change from a helicoidal path to a straight-line function during extension of the knee.

Although not limited to any particular theory, the ability of the knee brace of the present invention to withstand compression and distraction forces is believed to result from the stability imparted by the arrangement of the joint members in the mounting member. Although the mounting member has a structure which permits the joint member to control a complex polycentric motion, the mounting member also imparts stability to the joint members so as to substantially withstand compression and distraction forces thereby permitting the use of the joint in treating conditions of the knee which can benefit from both polycentric motion as well as compression or distraction of the knee joint.

DETAILED DESCRIPTION OF THE DRAWINGS

FIG. 15 is a perspective view of the tibial and femoral components when the knee is in extension.

FIG. 16 is a perspective view of the tibial and femoral components when the knee is in flexion at about 50°.

FIG. 17 is a perspective view of the tibial and femoral components when the knee is in flexion at about 90°.

DETAILED DESCRIPTION OF THE INVENTION

Figure 1:
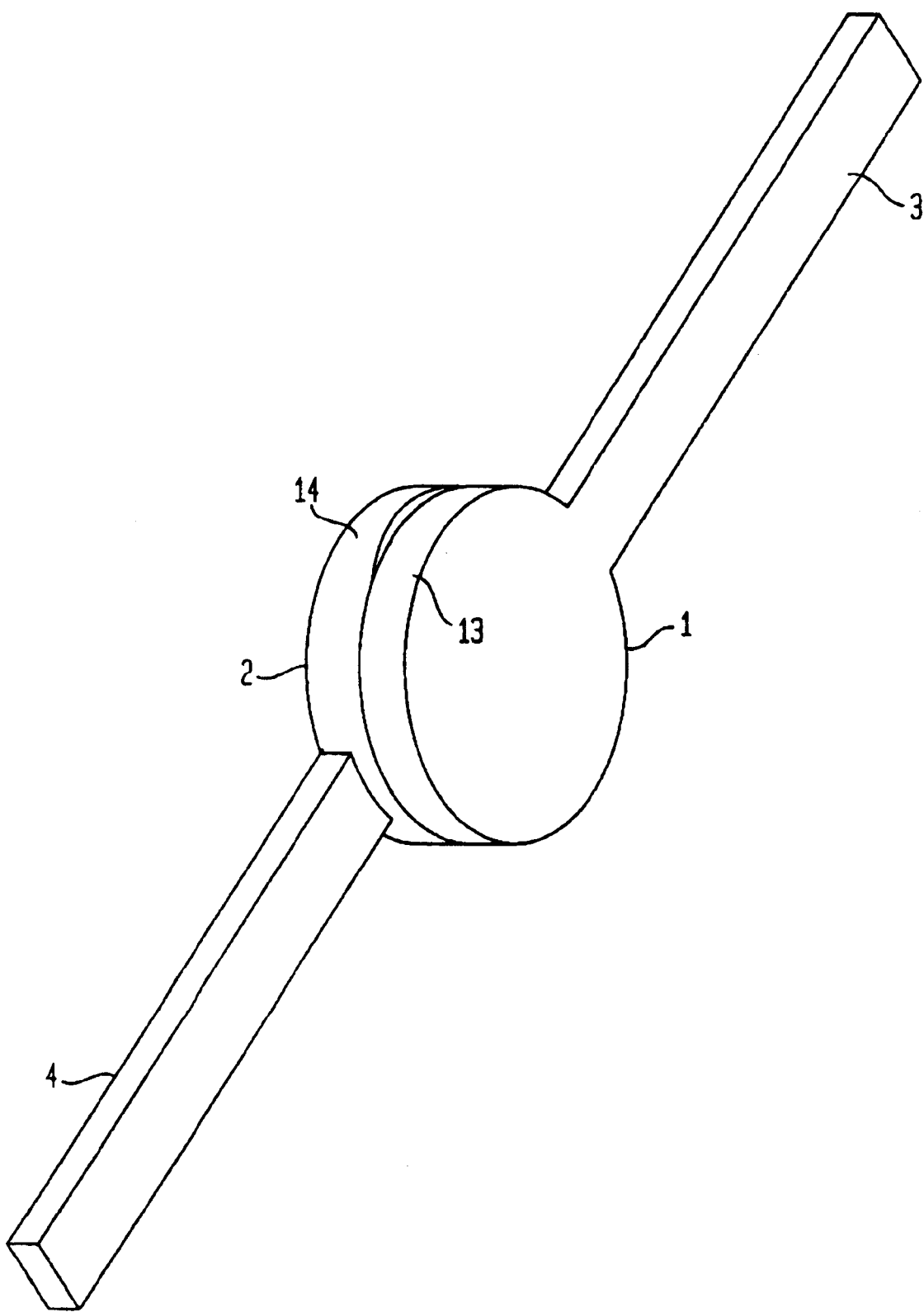
FIG. 1 is a perspective view of the tibial and femoral components of the joint of the present invention.
Figure 2:
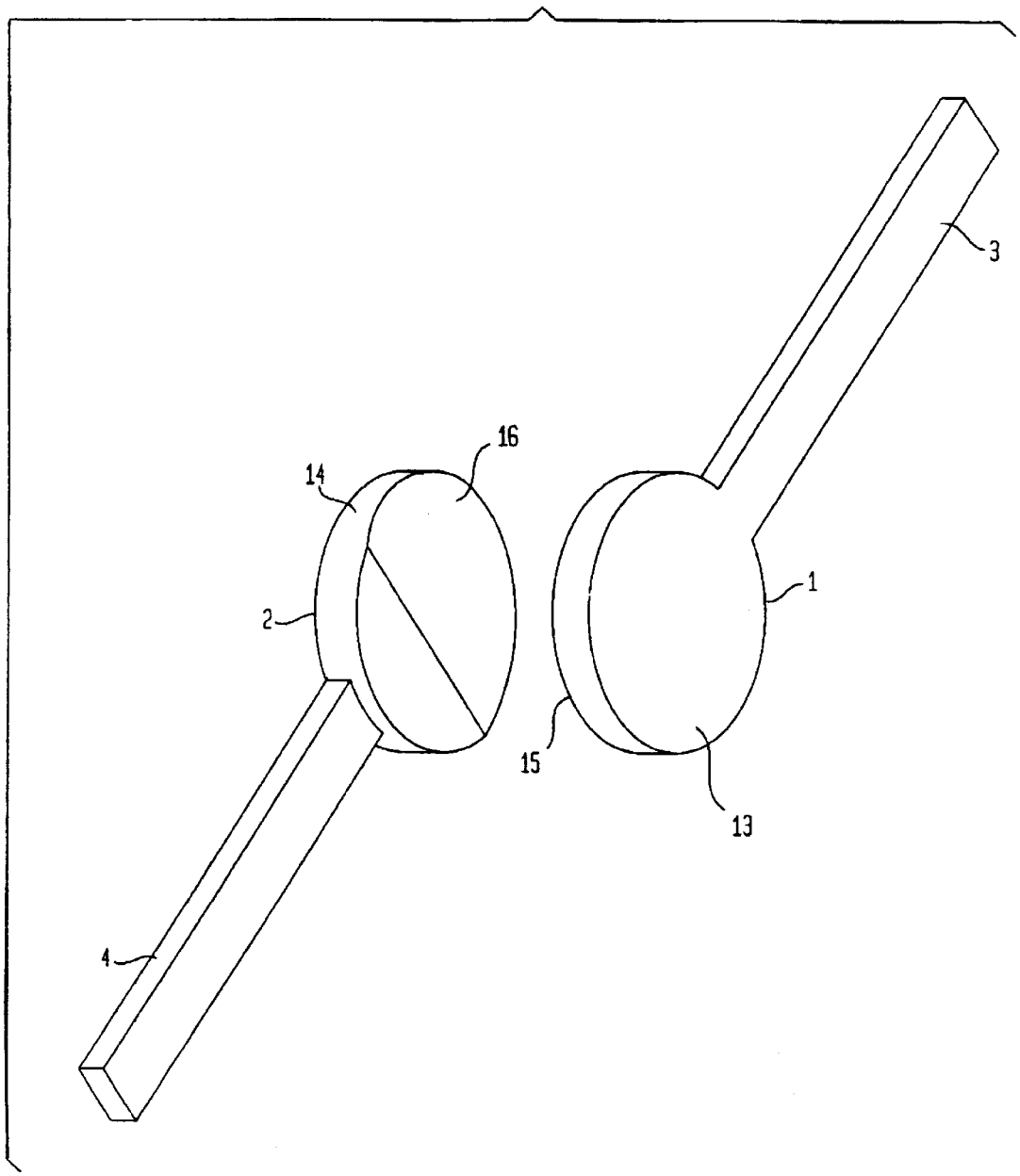
FIG. 2 is an exploded view of the tibial and femoral components of the joint of the present invention.

FIG. 1 shows a polycentric joint for use in a knee brace constructed according to the teachings of the present invention. The polycentric joint includes a femoral component 1 which includes a joint member 13 and a stem 3 projecting from joint member 13 for attaching femoral component 1 to the upper leg or femur, as described below. The polycentric joint further includes a tibial component 2 which includes a joint member 14 and a stem 4 projecting from joint member 14 for attaching tibial component 2 to the lower leg or tibia, as described below. The femoral and tibial joint members are preferably conical shaped or cylindrical. As shown in FIG. 2, femoral joint member 13 has at least one mating surface 15 which contacts at least one bearing surface 16 of tibial joint member component 14 when the components are in assembled relationship.

Figure 3:
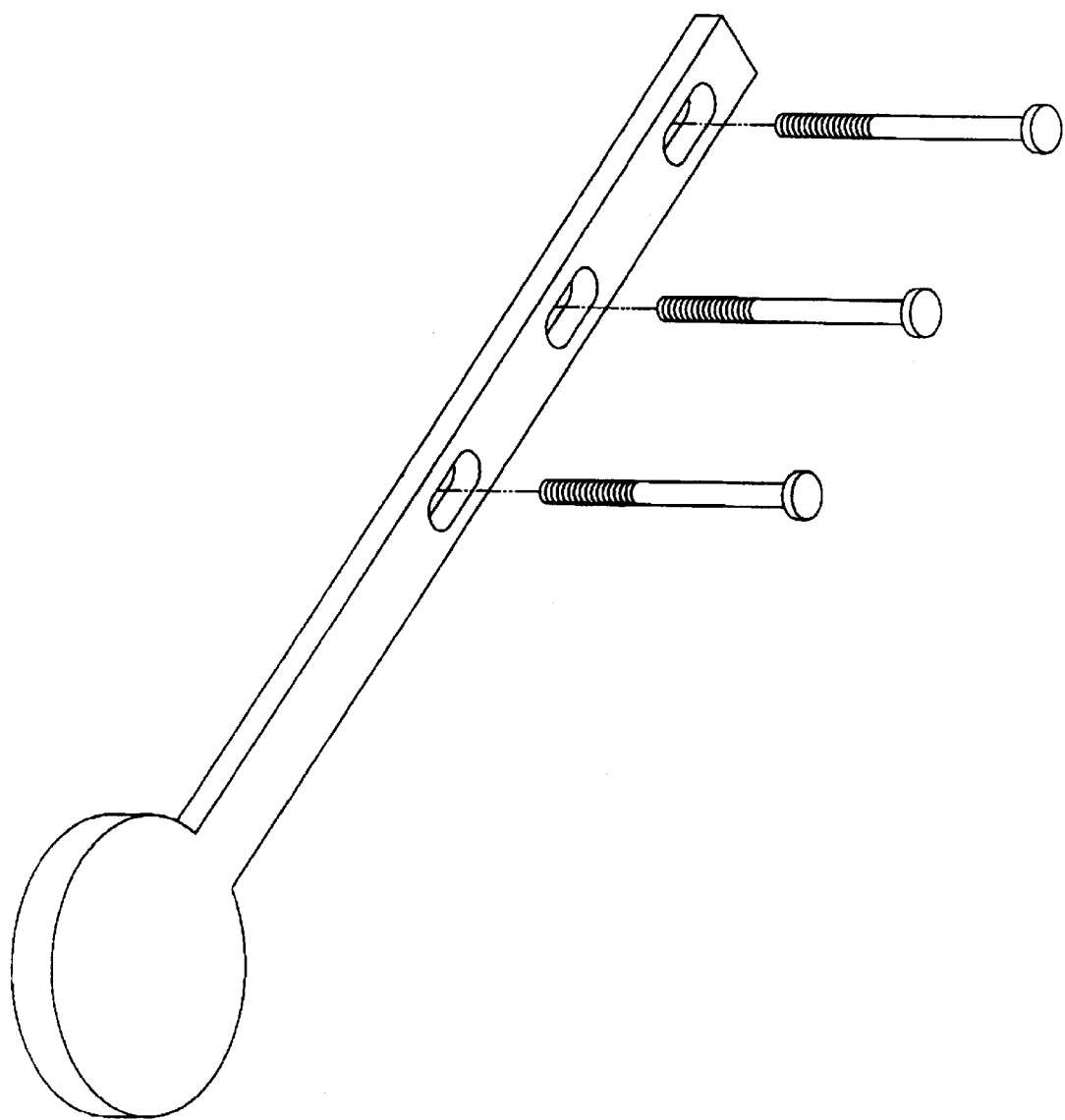
FIG. 3 is a perspective view of a femoral or tibial stem with apertures for receiving orthopedic bone screws.

The femoral stem 3 and tibial stem 4 are of sufficient length for securing the components to the upper and lower legs of a person, respectively. Depending on the purpose for which the knee brace is to be used, the stems may be attached to the leg using any suitable attachment, including belts, straps or Velcro®. Alternatively, as shown in FIG. 3, the femoral and tibial stems may have apertures 17 for receiving orthopedic bone screws 18 or other orthopedic fasteners for connecting the stems directly to the femur and tibia, respectively. Preferably, apertures 17 are nonspherical. More preferably, apertures 17 have an oval shape so as to permit distraction or compression of the knee, as described below.

Figure 4:
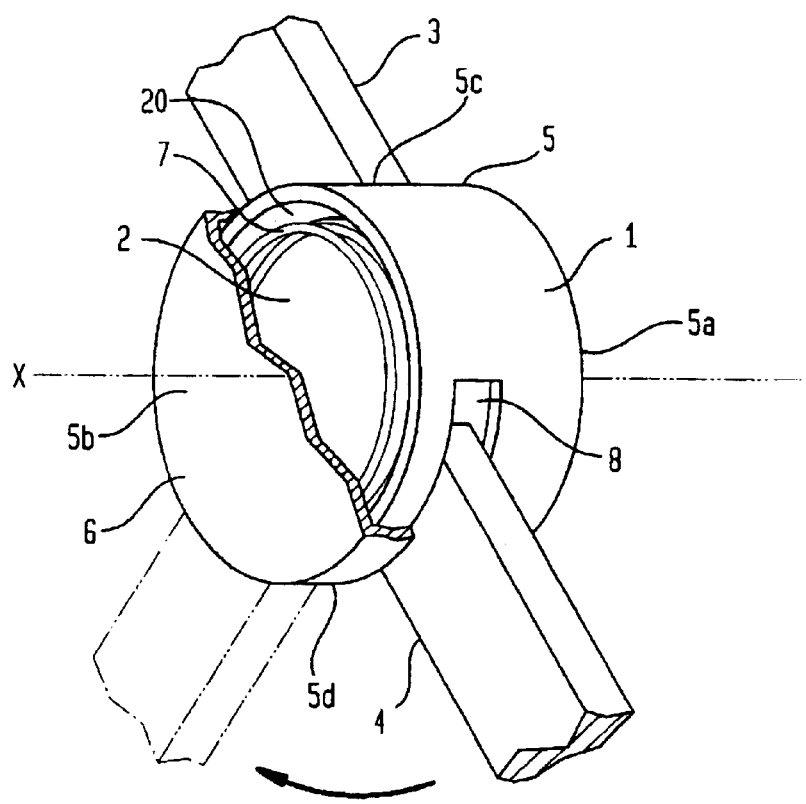
FIG. 4 is a perspective view of the joint of the present invention and shows the location of the tibial component in about the extension position and a phantom position of the tibial component in flexion at about 90°.
Figure 5:
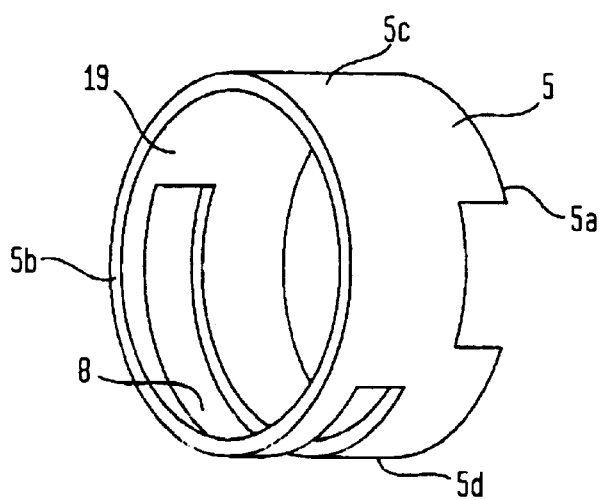
FIG. 5 is a perspective view of an example of a mounting member used in the joint of the present invention.

As shown in FIG. 4, femoral joint member 13 and tibial joint member 14 are arranged in assembled relationship within mounting member 5. Mounting member 5 preferably includes a hollow cylindrical or conical-shaped wall 19 having a first end 5a and a second end 5b. End 5b of the mounting member may be closed or partially closed, such as, for example, by a cap 6 connected by threaded engagement or otherwise to wall 19 of mounting member 5. Tibial joint member 14 and femoral joint member 13 are in juxtaposition in mounting member 5. Femoral joint member 13 is assembled in mounting member 5 so as to be fixed relative thereto, such as by screwing, welding, gluing or otherwise fixing joint member 13 relative to mounting member 5. In a more preferred arrangement, femoral joint member 13 may form end 5a of the mounting member. The tibial joint member 14 is rotatable relative to femoral joint member 13 within mounting member 5. More preferably, there is a small gap 20 between the outer circumference of tibial joint member 14 and the inner surface of wall 19 of mounting member 5 to enable the tibial joint member 14 to rotate freely within mounting member 5 relative to the femoral joint member. Gap 20 is preferably minimized so as to restrict movement of tibial joint member 14 in radial directions relative to rotation axis x. In a more preferred embodiment, gap 20 is about 1 mm.

Mounting member 5 further includes a spring 7 or other resilient member. Spring 7 biases the tibial joint member 14 towards femoral joint member 13 so that the bearing surface 16 of the tibial joint member is pressed against or confronts the mating surface 15 of the femoral joint member 13. Spring 7 is preferably located between end 5b of the mounting member and a surface of the tibial joint member which is opposite to the bearing surface of the tibial component.

As shown in FIG. 4, when tibial joint member 14 and femoral joint member 13 are in assembled relationship in mounting member 5, the tibial stem 4 preferably exits mounting member 5 through a slot 8 in wall 19 of the mounting member. Slot 8 permits tibial stem 4 to rotate as tibial joint member 14 rotates relative to fixed femoral joint member 13. Slot 8 also permits medial and lateral displacement of tibial stem 4 as defined by the interaction of the joint members. Preferably, slot 8 permits the rotation of the tibial stem 4 from about 0° to about 120° and about a 4–5 mm medial and lateral displacement of the tibial stem relative to the fixed femoral joint member 13 as a function of the angle of rotation of the knee.

The mating surface 15 of femoral joint member 13 has a predetermined contour. During flexion of the knee from the extension position shown in FIG. 15 to flexion positions, such as those shown in FIGS. 16 and 17, the bearing surface 16 of tibial joint member 14 follows the predetermined contour defined by the mating surface 15 of femoral joint member 13 resulting in displacement of the tibial joint member 14 away from femoral joint member 13 along rotation axis x. Spring 7 exerts a biasing force on tibial joint member 14 which permits tibial joint member 14 to move away from femoral joint member 13 along rotation axis x, but which assures that at least a portion of bearing surface 16 and mating surface 15 are in contact and the joint members are properly aligned, depending upon their relative rotational relationship. It will be appreciated that rotation from flexion to extension will cause tibial joint member 14 to move toward femoral joint member 13 along rotation axis x.

The displacement of the tibial component relative to the femoral component during flexion occurs in a helicoidal path, resembling a portion of a screw thread or a corkscrew. Accordingly, as shown in FIG. 15, in the extension position, tibial component 2 and femoral component 1 are aligned substantially parallel to plane y extending in an anterior posterior direction through the leg, referred to as the "neutral plane". As shown in FIGS. 16 and 17, during flexion, as tibial joint member 14 rotates relative to fixed femoral joint member 13, the tibial component 2 moves away from the fixed femoral component 1 and the neutral plane along rotation axis x.

The polycentric motion of the joint of the present invention also includes a change from an arc of motion to a neutral plane during extension of the knee. Thus, as the rotation of tibial component 14 is reversed during extension, tibial component 2 moves toward the fixed femoral component 1 and the neutral plane until the joint members are again aligned substantially parallel to each other and the neutral plane.

Figure 6:
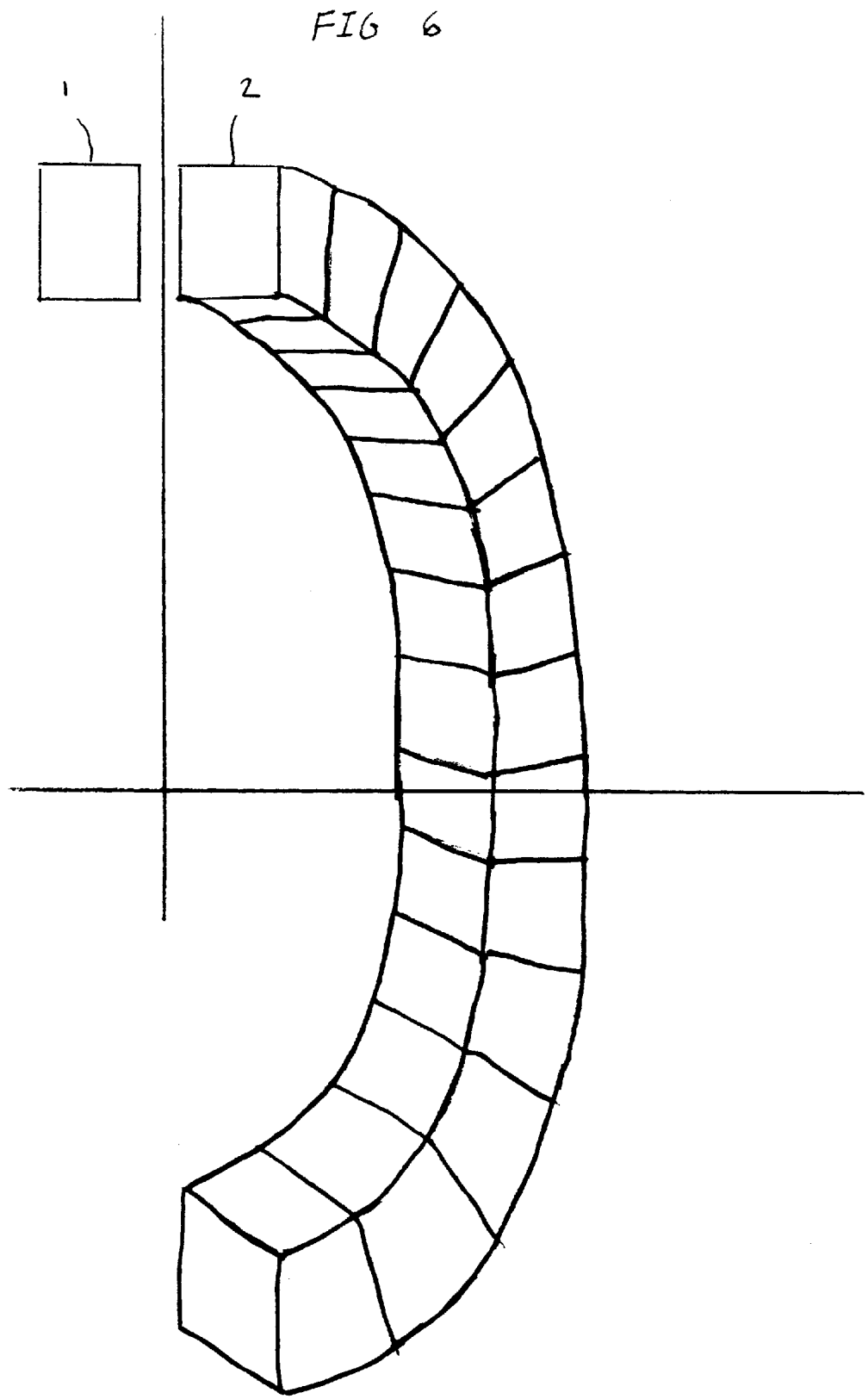
FIG. 6 is a graph illustrating the helicoidal motion of the tibial component of the joint of the present invention.
Figure 7:
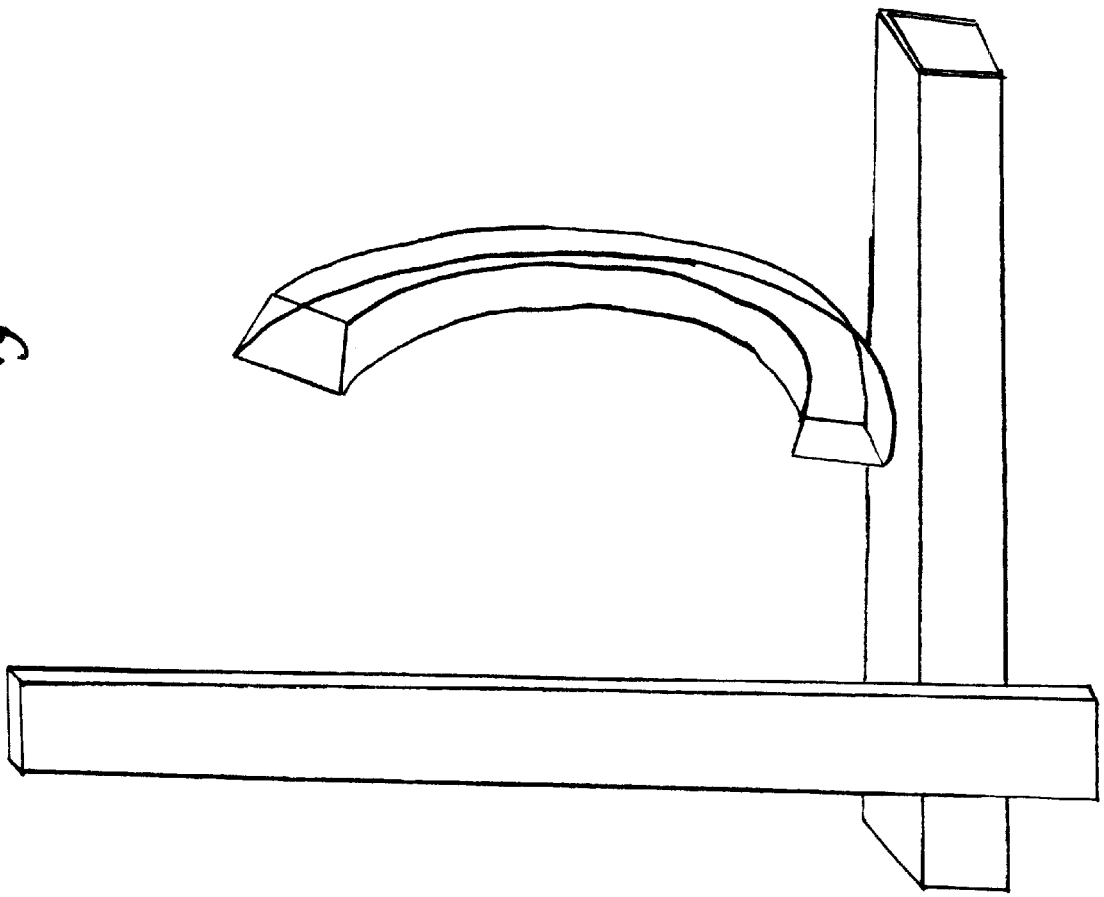
FIG. 7 is a graph illustrating the three dimensional motion of the tibial component of the joint of the present invention.
Figure 8:
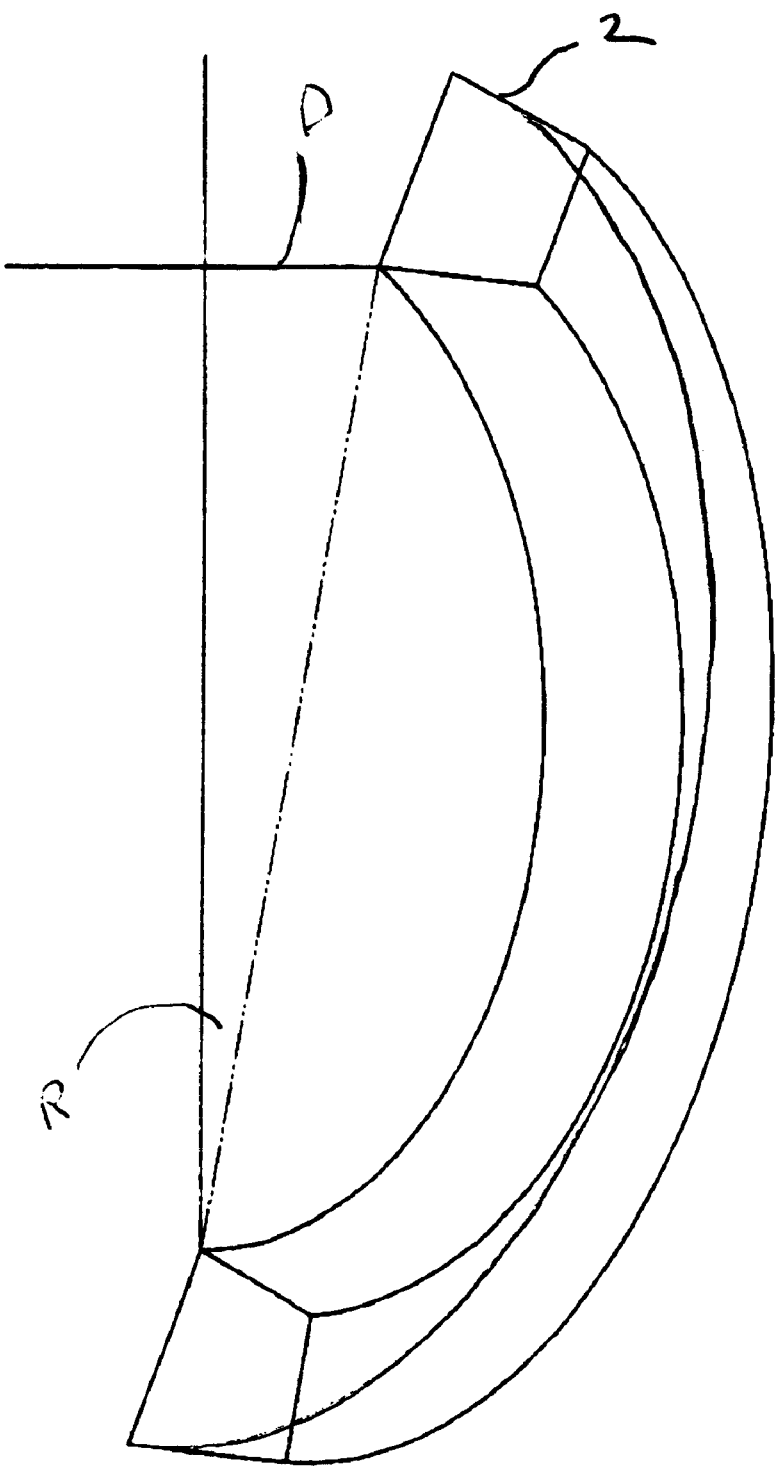
FIG. 8 is a graph illustrating the rise and displacement of the helicoidal path of motion of the tibial component relative to a neutral plane extending through the knee.

As used in accordance with the present invention, a "helicoidal path" refers to a path of motion which is generally helical. Examples of the helicoidal path defined by the present invention are shown in FIGS. 6 and 7, and can be determined from measurements of physiological knee motion using any suitable model known in the art. Suitable models, include, for example, biomechanical models, such as those produced by computer aided design, mathematical models, and physiological measurements taken from human cadavers and healthy individuals. Preferably, physiological motion is determined using the apparatus described in U.S. Pat. No. 5,928,234, the disclosure of which is incorporated by reference herein. As shown in FIG. 8, in a more preferred embodiment, the helicoidal path of motion controlled by the joint of the present invention includes maximal medial displacement D of the tibia relative in the femur of about 4 mm to about a 5 mm which includes about a 7° to about 8° rise R of the helicoid. The maximal medial displacement and rise occur during flexion of the knee from about 50° to about 120°.

Figure 9:
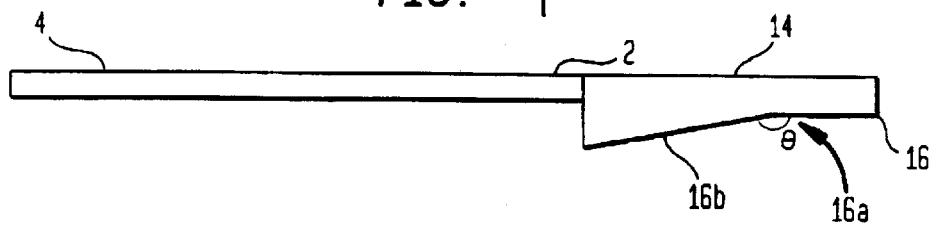
FIG. 9 is a perspective view of a variant of the tibial component of the joint of the present invention.
Figure 10:
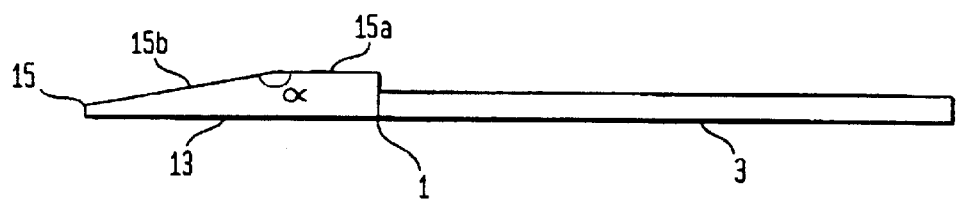
FIG. 10 is a perspective view of a variant of the femoral component of the joint of the present invention.
Figure 11:
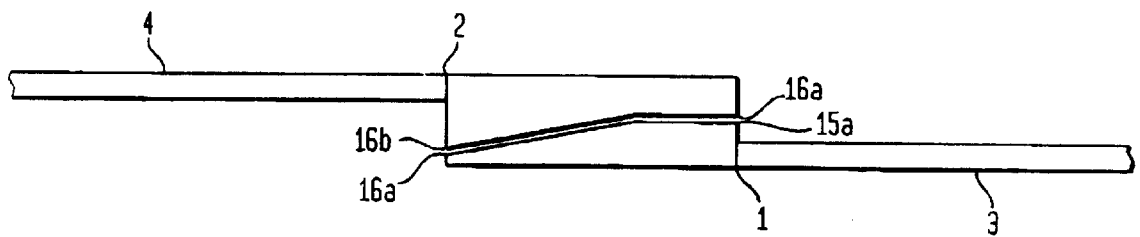
FIG. 11 is a perspective view showing the alignment of the tibial and femoral components when the knee is in extension.
Figure 12:
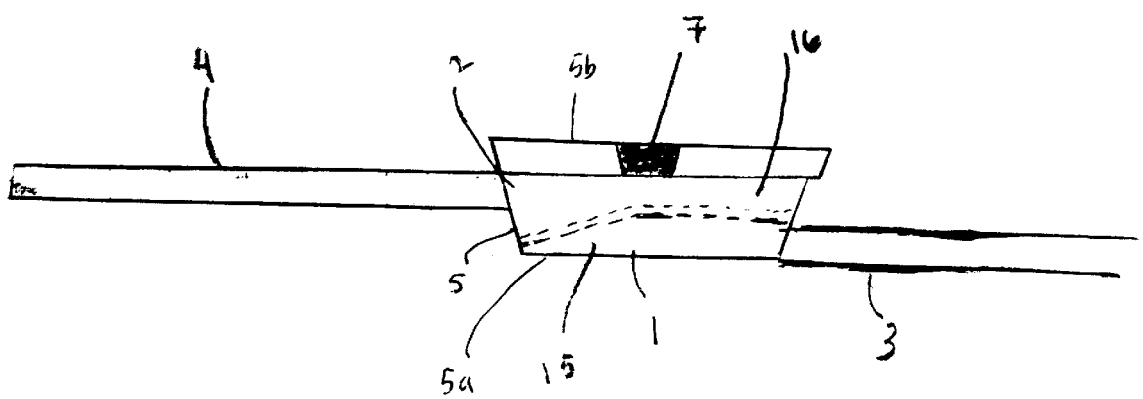
FIG. 12 is a perspective view of a variant of the tibial component of the joint of the present invention.

The displacement of the tibial component 2 relative to the femoral component 1 results from the camming action of the confronting surfaces of the joint members, as a function of the rotation of the tibial component relative to the femoral component. The desired displacement can result from various confronting surface designs of the joint members, and the present invention is not limited to any particular design disclosed herein. In a preferred embodiment, as shown in FIG. 9, the bearing surface 16 of the tibial joint member 14 has a first surface 16a and a second surface 16b. Second surface 16b is at obtuse angle θ to first surface 16a. As shown in FIG. 10, mating surface 15 of the femoral joint member 13 has complementary surfaces. In particular, the mating surface 15 consists of a first surface 15a and a second surface 15b at angle α which is obtuse relative to the first surface 15 and approximately equal to angle θ. As shown in FIG. 11, when the knee is in extension, surface 16a lies substantially parallel to surface 15a, and concomitantly, surface 16b lies substantially parallel to surface 15b, such that there is little, if any, displacement of the tibial component 2 relative to the fixed femoral component 1 along rotation axis x. When the tibial component 2 is rotated relative to the femoral component 1 along positions on an arc of motion from about 0° to about 120°, first surface 16a of the tibial joint member 14 follows the path defined by second surface 15b of the femoral joint member 13, resulting in displacement of tibial component 2 away from femoral component 1 along the rotation axis x as shown in FIGS. 16 and 17.

Figure 13:
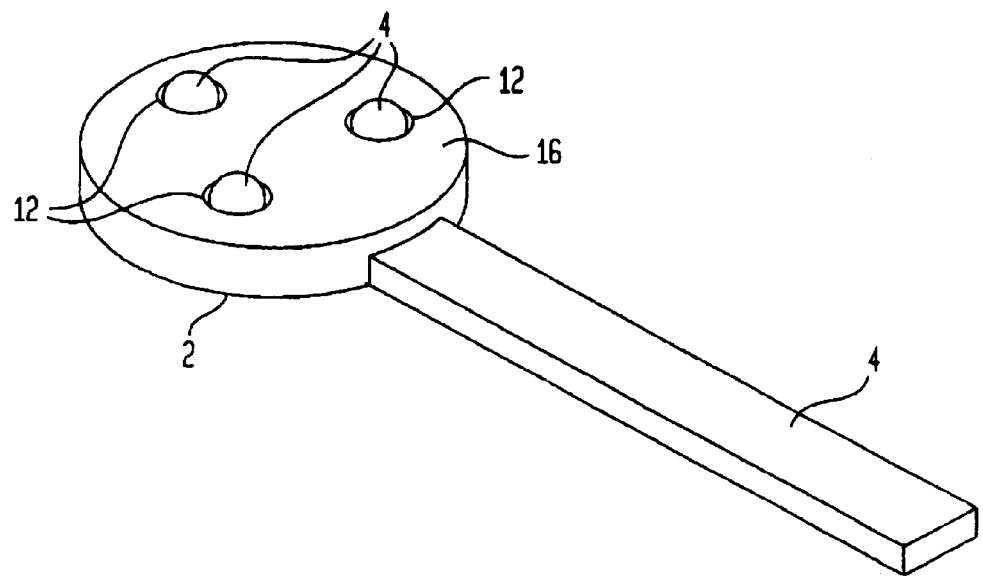
FIG. 13 is a side elevation view illustrating the arrangement of the joint members and mounting member.
Figure 14:
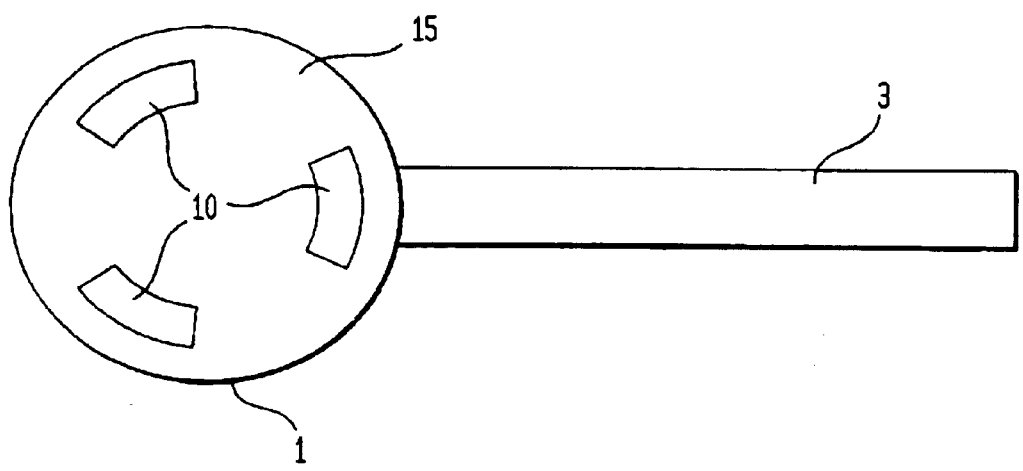
FIG. 14 is a perspective view of a variant of the femoral component of the joint of the present invention.
Figure 18:
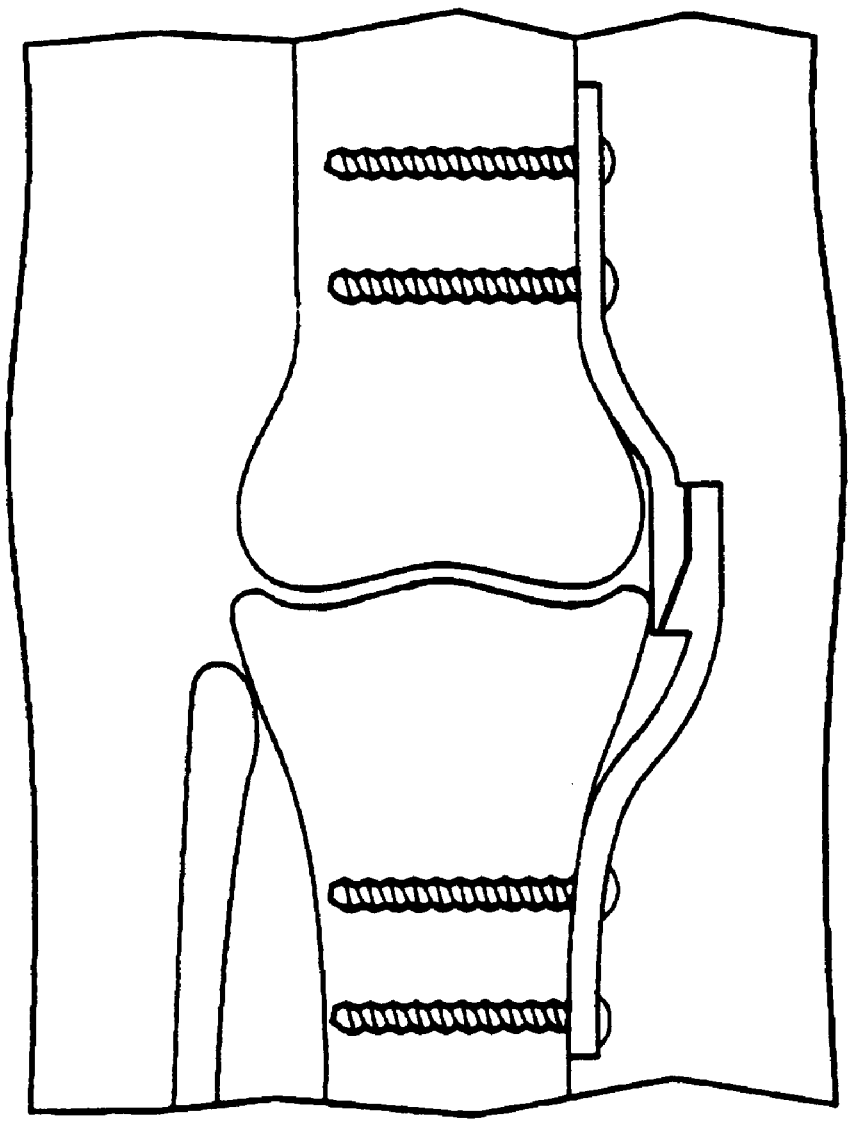
FIG. 18 shows the internal attachment of the joint of the present invention to the leg of a patient using orthopedic bone screws.

As shown in FIG. 13, in another preferred embodiment, bearing surface 16 of tibial joint member 14 is a substantially planar surface having at least one ball bearing 11 arranged in a corresponding socket 12 located in the substantially planar bearing surface. A portion of the ball bearing 11 extends above the substantially planar bearing surface 16 of the tibial joint member 14 for contact with the mating surface 15 of the femoral joint member 13. As shown in FIG. 14, the mating surface 9 of the femoral joint member 13 consists of at least one ramp 10 having a predetermined contour or path which mates with a corresponding ball bearing 11 on the tibial joint member 14. When the knee is extended, the ball bearing is near the bottom of the ramp so that the mating surface and the bearing surface are aligned substantially parallel to each other, and there is little, if any, displacement of the tibial component 2 relative to the femoral component 1. During flexion of the knee, the ball bearing 11 of the tibial joint member 14 follows the ramp 12 of the femoral joint member 13. Thus, when the tibial component 2 is rotated relative to the femoral component 1 along positions on an arc of motion from about 0° to about 120°, the ball bearing 11 follows the path defined by the ramp 10, resulting in displacement of the tibial component 2 away from the femoral component 1 along rotation axis x as a function of the angle of rotation.

Any suitable mounting member may be used in the joint of the present invention. In another preferred embodiment the mounting member is a housing. In yet another embodiment of the present invention, the mounting member includes a wall which is arranged parallel to and rigidly connected to the femoral component. The tibial joint member is connected to the wall by at least one spring clamp which biases the tibial component towards the femoral component so that the bearing surface of the tibial joint member is pressed against or confronts the mating surface of the femoral joint member. A second spring clamp or a series of spring clamps may also be used to restrict the movement of the tibial joint member in radial directions relative to rotation axis x.

Materials suitable for use in the joint preferably include materials that provide low friction, including, for example, metal, high-density polyethylene and the like. In addition to the low-friction materials, the surfaces of the components can be coated to reduce the coefficient of friction. If used in an internal brace, the materials of the components must also be biocompatible. Suitable biocompatible materials include stainless steel, polyethylene, CoCR and combinations thereof.

The polycentric joint of the present invention can be used in any knee brace, including an internal knee brace, an external knee brace or an external fixator. The polycentric joint of the present invention is also suitable for use in a knee brace for treatment of conditions of the knee which can benefit from both polycentric motion and compression or distraction of the knee.

Accordingly, in a preferred embodiment, the joint of the present invention is used in a knee brace to treat unicompartment osteoarthritis, such as medial joint osteoarthritis with medial joint cartilage loss and often bone spur formation. Joint pain suffered by these patients following surgery can be substantially alleviated by the use of the knee brace of the present invention which permits both polycentric movement of the knee and distraction of the joint.

In another preferred embodiment, the joint of the present invention is used in cartilage grafts in which there has been joint incongruity and joint compression, and in which the graft site can benefit from both distraction and polycentric joint motion.

In yet another preferred embodiment, the joint of the present invention is used in a knee brace for treating lateral or medial ligament tears of the knee in which there has been gapping of the joint and in which it is desired to compress the joint and at the same time permit joint motion.

Figure 19:
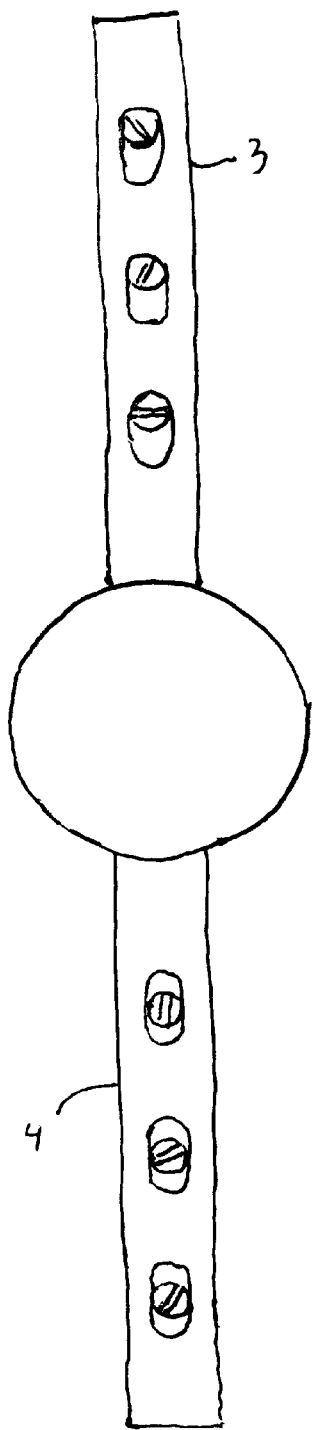
FIG. 19 is a perspective view of the femoral and tibial stems which shows the placement of the orthopedic bone screws in the apertures of the femoral or tibial stem during distraction of the knee joint.

Distraction or compression of the knee joint can be accomplished in accordance with the present invention by positioning the knee in an extension or distraction position and then inserting orthopedic bone screws eccentric to the center of the apertures of the femoral and tibial stems. As shown in FIG. 19, during distraction of the knee, the tibial component is preferably fixed to the tibia first with centrally located screws. Following fixation of the tibial component, the femoral stem is fixed to the femur by placing the screws eccentic to the aperture of the femoral stem which forces the knee to distract.

It is to be understood that the above-detailed description of the preferred embodiment of the invention is provided by way of example only. Various details of the design and construction may be modified without departing from the scope of the invention as set forth in the claims. In addition, the invention will be further described by reference to the following detailed examples. These examples are merely illustrative and not limitative of Applicant's invention in any way.

EXAMPLE 1

Determination of Knee Joint Motion

A three-dimensional pattern of motion of the knee was obtained using the apparatus described in U.S. Pat. No. 5,928,234. The pattern formed in a clay model was an arc of movement, which approximates a scythe or sickle shape. With extension of the knee, a straight-line function in the model resulted, i.e., there was no change in the plane or inclination of that function. With the bending of the knee, i.e., to 45° and 90°, a change in direction occurred to form a 90° arc. With this change of direction, there was also a change in the inclination (i.e., depth) of the pattern from about 7° to about 8° which was determined to be about 4 mm to about 5 mm. In terms of geometric forms that are appreciated by reviewing this pattern, there is a circular movement with a straight-line function, in which the straight-line function is equivalent to the extension of the knee and the 90° arc of motion in the circle is equivalent to a 90° bend of the knee. Thus, when the knee bends from 45° to 90°, an internal rotation of the tibia and a medial displacement of the tibia relative to the femur occurred, which was characterized by a 4 mm to 5 mm depth in the pattern associated with a 7° to 8° inclination. With extension of the knee, there was a lateral displacement of the tibia with a change of inclination of the arc of motion to a neutral plane defined by a straight-line function.

EXAMPLE 2

Construction of the Polycentric Joint

A polycentric joint was created to control a 4 mm to 5 mm medial and lateral displacement as well as an inclination of 7° to 8° with a 90° to about 120° arc of motion during flexion and to account for the change of plane of arc of motion to a neutral plane during extension. The femoral component was a cylindrical component having a diameter of about 40 mm. An angle of inclination of about 6° to about 8° was produced on the surface of the cylindrical component beginning at outermost point of the cylinder at a height of about 1 mm. The angle of inclination plateaued at 25 mm from the outermost point at a height of 5 mm. The tibial component had a complimentary cylindrical bearing surface having a diameter of 40 mm. An angle of inclination of about 6° to about 8° was produced on the surface beginning at the innermost point of the cylindrical surface at a height of about 9 mm and plateaued at 25 mm from the innermost point at a height of 4 mm. The components were then arranged in a cylindrical housing. The femoral component was fixed at one end of the housing.

I claim:

1. A knee brace comprising:

a femoral component including a femoral joint member having a first mating surface and a second mating surface arranged at a first obtuse angle to said first mating surface, said femoral component further including a stem projecting from said femoral joint member for attachment to the upper leg of a patient so as to fix said femoral component relative to said upper leg;

a tibial component including a tibial joint member having a first bearing surface and a second bearing surface arranged at a second obtuse angle to said first bearing surface; said first and second bearing surfaces being in contact respectively with said first and second mating surfaces of said femoral joint member, said first bearing surface of said tibial joint member being complementary to said first mating surface of said femoral joint member and said second bearing surface of said tibial joint member being complementary to said second mating surface of said femoral joint member; and wherein said tibial component further includes a stem projecting from said tibial joint member for attachment to the lower leg of the patient so as to fix said tibial component relative to said lower leg;

a mounting member, said femoral joint member and said tibial joint member being arranged in juxtaposition in said mounting member, wherein said first and second bearing surfaces of said tibial joint member are in contact with said first and second mating surfaces of said femoral joint member, wherein at least a portion of said femoral joint member is fixed to said mounting member, and wherein said tibial component is rotatable relative to said femoral joint member; and a resilient member, said resilient member being arranged between an inner surface of said mounting member and said opposite surface of said tibial joint member to bias said tibial joint member toward said femoral joint member.

2. The knee brace of claim 1, wherein said first and second obtuse angles are approximately equivalent to each other.

3. The knee brace of claim 1 wherein said mounting member includes a hollow cylindrical or conical-shape wall having a first end and a second end.

4. The knee brace of claim 3 wherein said mounting member includes a slot whereby said tibial stem exits said mounting member through said slot.

5. The knee brace of claim 3, including a cap at said second end of said mounting member.

6. The knee brace of claim 3 wherein a gap exists between an outer circumference of said tibial joint member and said hollow cylindrical or conical-shape wall of said mounting member.

7. The knee brace of claim 1 wherein said resilient member is a spring.

8. The knee brace of claim 1 wherein said femoral and tibial stems contain apertures for receiving orthopedic bone screws.

9. The knee brace of claim 1, wherein the tibial component and femoral component are arranged and constructed in such a way that the knee joint is continually distracted.

10. The knee brace of claim 1, wherein the tibial component and femoral component are arranged and constructed in such a way that the knee joint is continually compressed.

11. A knee brace comprising:

a femoral component including a femoral joint member having a first mating surface and a second mating surface arranged at a first obtuse angle to said first mating surface, said femoral component further including a stem projecting from said femoral joint member for attachment to the upper leg of a patient so as to fix said femoral component relative to said upper leg;

If a tibial component including a tibial joint member having a first bearing surface and a second bearing surface arranged at a second obtuse angle to said first bearing surface; said first and second bearing surfaces being in contact respectively with said first and second mating surfaces of said femoral joint member, said first bearing surface of said tibial joint member being complementary to said first mating surface of said femoral joint member and said second bearing surface of said tibial joint member being complementary to said second mating surface of said femoral joint member; and wherein said tibial component further includes a stem projecting from said tibial joint member for attachment to the lower leg of the patient so as to fix said tibial component relative to said lower leg;

a mounting means for receiving said femoral joint member and said tibial joint member, wherein at least a portion of said femoral joint member is fixed to said mounting means and said tibial component is rotatable relative to said femoral joint member within said mounting means, and wherein said femoral joint member and said tibial joint member are in juxtaposition and aligned on opposite sides of a vertical, anterior-posterior plane; and a resilient means for biasing said tibial joint member toward said femoral joint member.

12. The knee brace of claim 11, wherein said first and second obtuse angles are approximately equivalent to each other.

13. The knee brace of claim 11 wherein said mounting means is a hollow cylindrical or conical-shape wall.

14. The knee brace of claim 11 wherein said mounting means is a housing.

15. The knee brace of claim 11 wherein said resilient means is a spring.

16. The knee brace of claim 11 wherein said mounting means includes a slot whereby said tibial stem exits said mounting means through said slot.

17. The knee brace of claim 11 wherein said femoral and tibial stems contain apertures for receiving orthopedic bone screws.

18. The knee brace of claim 11, wherein the tibial component and femoral component are arranged and constructed in such a way that the knee joint is continually distracted.

19. The knee brace of claim 11, wherein the tibial component and femoral component are arranged and constructed in such a way that the knee joint is continually compressed.

* * * * *